United States Patent
Lewis

(10) Patent No.: US 8,993,288 B2
(45) Date of Patent: *Mar. 31, 2015

(54) METHOD FOR CONVERTING BIOMASS TO METHANE

(71) Applicant: Anaergia Inc., Burlington (CA)

(72) Inventor: F. Michael Lewis, El Segundo, CA (US)

(73) Assignee: Anaergia Inc., Burlington (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/031,758

(22) Filed: Sep. 19, 2013

(65) Prior Publication Data

US 2014/0024096 A1 Jan. 23, 2014

Related U.S. Application Data

(63) Continuation of application No. 13/136,180, filed on Jul. 26, 2011, now Pat. No. 8,877,468.

(60) Provisional application No. 61/404,005, filed on Sep. 24, 2010.

(51) Int. Cl.
| | |
|---|---|
| C12P 7/10 | (2006.01) |
| C10B 47/44 | (2006.01) |
| C10B 53/02 | (2006.01) |
| C10C 5/00 | (2006.01) |
| C10L 3/08 | (2006.01) |
| C12P 5/02 | (2006.01) |
| C12P 7/08 | (2006.01) |
| C12P 7/14 | (2006.01) |

(52) U.S. Cl.
CPC . *C12P 7/14* (2013.01); *C10B 47/44* (2013.01); *C10B 53/02* (2013.01); *C10C 5/00* (2013.01); *C10L 3/08* (2013.01); *C12P 5/023* (2013.01); *C12P 7/08* (2013.01); *C12P 7/10* (2013.01); *Y02E 50/14* (2013.01); *Y02E 50/16* (2013.01); *Y02E 50/32* (2013.01); *Y02E 50/343* (2013.01)
USPC ...................................................... 435/165

(58) Field of Classification Search
USPC ............ 435/165; 201/2.5; 585/240; 481/275
See application file for complete search history.

(56) References Cited

U.S. PATENT DOCUMENTS

| | | | |
|---|---|---|---|
| 4,289,625 | A | 9/1981 | Tarman et al. |
| 4,880,473 | A | 11/1989 | Scott et al. |
| 5,395,455 | A | 3/1995 | Scott et al. |
| 5,417,492 | A | 5/1995 | Christian et al. |
| 5,424,417 | A | 6/1995 | Torget et al. |
| 5,605,551 | A | 2/1997 | Scott et al. |
| 5,865,898 | A | 2/1999 | Holtzapple et al. |
| 5,959,167 | A | 9/1999 | Shabtai et al. |
| 6,022,419 | A | 2/2000 | Torget et al. |
| 6,048,374 | A | 4/2000 | Green |
| 6,228,177 | B1 | 5/2001 | Torget |
| 7,494,637 | B2 | 2/2009 | Peters et al. |
| 7,578,927 | B2 | 8/2009 | Marker et al. |
| 7,608,439 | B2 | 10/2009 | McTavish et al. |
| 7,972,824 | B2 | 7/2011 | Simpson et al. |
| 8,383,871 | B1 | 2/2013 | Sellars et al. |
| 2007/0117195 | A1 | 5/2007 | Warner et al. |
| 2007/0217995 | A1 | 9/2007 | Matsumura et al. |
| 2008/0236042 | A1 | 10/2008 | Summerlin |
| 2009/0151253 | A1 | 6/2009 | Manzer et al. |
| 2009/0229595 | A1 | 9/2009 | Schwartz |
| 2009/0239279 | A1 | 9/2009 | Hall et al. |
| 2010/0133085 | A1 | 6/2010 | Hutchins et al. |
| 2010/0317070 | A1 | 12/2010 | Agaskar |
| 2011/0033908 | A1 | 2/2011 | Cheong et al. |
| 2011/0179700 | A1 | 7/2011 | Monroe et al. |
| 2011/0248218 | A1 | 10/2011 | Sutradhar et al. |

FOREIGN PATENT DOCUMENTS

| | | |
|---|---|---|
| BR | PI009401102-8 A | 8/1994 |
| CA | 2628323 | 6/2007 |
| CA | 2641270 | 12/2009 |
| JP | 2003089793 | 3/2003 |
| WO | 2004060587 | 7/2004 |
| WO | 2010001137 | 1/2010 |
| WO | 2012166771 A2 | 12/2012 |
| WO | 2012166771 A3 | 12/2012 |
| WO | 2013110186 | 8/2013 |

OTHER PUBLICATIONS

Demirbas, A., "The influence of temperature on the yields of compounds existing in bio-oils obtained from biomass samples via pyrolysis", Fuel Processing Technology, 2007, vol. 88, pp. 591-597.
Demirbas, A., "Biomass resource facilities and biomass conversion processing for fuels and chemicals", Energy Conversion & Management, 2001, vol. 42, pp. 1357-1378.
Gullu, D., et al., "Biomass to methanol via pyrolysis process", Energy Conversion & Management, 2001, vol. 42, pp. 1349-1356.
Melin, K., et al., "Evaluation of lignocellulosic biomass upgrading routes to fuels and chemicals", Cellulose Chemistry and Technology, 2010, vol. 44, No. 4-6, pp. 117-137.
AWWTA, Standard Methods, Section 240G, 2000.

*Primary Examiner* — Ralph Gitomer
(74) *Attorney, Agent, or Firm* — Scott Pundsack; Borden Ladner Gervais LLP

(57) ABSTRACT

A method for enhancing the treatment of lignocellulose-containing materials by biotreatment wherein such lignocellulose-containing materials, normally resistant to biotreatment, are first subjected to a low-temperature, long-residence time pyrolysis at about 175° C. to about 325° C. for about 0.1 hour to about 2.0 hours, wherein a substantial portion of the incoming material is distilled into water-soluble compounds amenable to anaerobic biotreatment. Exemplary applications of the method include pyrolytic pre-treatment of wastewater sludges, cellulosic wastes, wood, peat, plant residues, low-grade coal, and the like to enhance methane gas production in anaerobic digestion and/or oxygen-limited or oxygen-starved fermentation to produce ethanol.

15 Claims, 4 Drawing Sheets

(56) References Cited

OTHER PUBLICATIONS

ASTM, Section D3172, Proximate Analsys of Coal and Coke, 2007.
http://www.coskate.com/.coskata_Inc.
http://www.ineosbio.com/57-welcometoINEOSBio.htm.
International Search Report of PCT/CA2013/050037 dated Apr. 4, 2013.
Excerpts from Traite De Polarimetrie, Georges Bruhat, Paris, France, 1930.
Laemsak, Nikhom, Wood Vinegar presentation, Undated.
Lian, Jieni et al., Separation, hydrolysis and fermentation of pyrolytic sugars to produce ethanol and lipids, Bioresource Technologyvol. 101 (Dec. 2010), pp. 9688-9699.
Guiot, S.R. et al. (Mar. 2011), Potential of wastewater-treating anaerobic granules for biomethanation of synthesis gas, Environmental Science and Technology, vol. 45, Issue 5, pp. 2006-2012.
Bredwell, M.D., et al., (1999), Reactor Design Issues for Synthesis-Gas Fermentations, Biotechnology Process, vol. 15, Issue 5, pp. 834-844.
Cozzani et al., A fundamental study on conventional pyrolysis of a refuse-derived fuel, Ind. Eng. Chem. Res. 1995, 34, 2006-2020.
Jones, S. B. et al.: 'Production of Gasoline and Diesel from biomass via Fast Pyrolysis' Hydrotreating and Hydrocracking: A Design Case, U.S. Department of Energy, PNNL-18284 Feb. 28, 2009.
Lewis, F.M, et al.; A Powerful byproduct, WEFTEC, Jan. 2008, pp. 64-69.
Yang, Bin et al.; Pretreatment: the key to unlocking low-cost cellulosic ethanol, Biofuels, Bioprod. Bioref. 2:26-40 (2008).
Liaw, Shi-Shen et al.; Effect of pyrolysis temperature on the yield and properties of bio-oils obtained from the auger pyrolysis of douglas fir wood, Journal of Analytical and Applied Pyrolysis, vol. 93, Jan. 2012, pp. 52-62.
Shanley Pump and Equipment, Inc., EDUR Pumps, http://www.shanleypump.com/edur_pumps.html, printed May 30, 2014.
Mahulkar, A.V. et al; Steam Bubble Cativation, AlChE Journal, vol. 54, Issue 7, pp. 1711-1724, Jul. 2008.
Laird, David A. et al., Sustainable Alternative Fuel Feedstock Opportunities, Challenges and Roadmaps for Six U.S. Regions; Chapter 16: Pyrolysis and Biochar—Opportunities for Distributed Production and Soil Quality Enhancement, Proceedings of the Sustainable Feedstocks for Advance Biofuels Workshop, Atlanta, GA, Sep. 28-30, 2010 pp. 257-281.

METHOD FOR CONVERTING BIOMASS TO METHANE

This application is a continuation of U.S. application Ser. No. 13/136,180 filed on Jul. 26, 2011, now allowed which claims the benefit of U.S. Provisional Application No. 61/404,005 filed on Sep. 24, 2010, both of which are incorporated by reference.

BACKGROUND OF THE INVENTION

1. Field of the Invention

The present invention relates generally to energy conversion processes. More particularly, the invention pertains to methods for converting ligno-cellulosic materials resistant to biotreatment into materials which are highly amenable to biotreatment processes for forming energetic fuels in gaseous and/or liquid states.

2. State of the Art

In a long-standing wastewater treatment method commonly known as anaerobic digestion, anaerobic life forms convert a portion of the "volatile" materials in municipal wastewater sludge into a digester gas. Typically, less than about 50 percent of the volatile material in the sludge is converted to digester gas, a useful fuel largely comprised of methane ($CH_4$) and carbon dioxide ($CO_2$), typically in about a 63:35 proportion. Inasmuch as the ultimate goal is complete elimination of the volatiles in the sludge, a large portion of the volatile solids is disposed of in some other way, e.g. burning or landfill. This presents special and unique problems in California and other states that impose de-facto bans against thermal processes (e.g. combustion) For waste-to-energy (WTE) conversion.

The definition of "volatiles" used in wastewater treatment is found in Standard Methods 2540 G, wherein the "volatiles" analysis comprises the solids loss upon volatilization and combustion of a solids sample ignited at 500° C.

To those skilled in the art, it is apparent that anaerobic digestion should be theoretically applicable to the treatment of many other materials including for example, animal wastes, fats, oils, greases, plant materials, municipal solid wastes (MSW), wood, low-rank coal, lignite, and the like. While anaerobic digestion has been generally successful for hydrocarbon materials, i.e. oils and greases, such treatment of ligno-cellulosic materials has resulted in very slow and incomplete conversion. Because of the huge supply of such materials found in wastes and renewable resources, the need for methods to convert such materials into useable energetic products at high yield is readily evident. Such methods would also greatly reduce the need for landfilling of solid waste materials as is done currently.

More recently, efforts at producing methane from specific raw materials by utilizing various treatment steps (including anaerobic digestion) has resulted in the use of the term "biomethanation" to broadly describe such processes.

It is generally known that a substantial portion of the volatile materials in sewage sludge which are resistant to biomethanation typically comprise cellulosic lignins. These materials are very recalcitrant to biodegradation in part because they have a very low water-solubility.

Another disadvantage of conventional biomethanation is the low rate at which many non-lignic components become dissolved to become amenable to biological conversion. In the treatment of municipal wastewater sludges for example, this necessitates the use of very large digesters, as is well known in the waste treatment field. Yet, about one-half or more of the volatiles remain unconverted and must be disposed of in some other way. A method for enabling complete rapid conversion of volatile materials in the digester would be extremely beneficial in several ways. First, the amount of sludge solids which must be ultimately disposed of by landfill or out-of-state waste-to-energy facilities is reduced. Secondly, the quantity of digester gas with valuable heating value is simultaneously increased. A further possible benefit is a reduction in the required digestion residence time, which will increase the capacity of in-place digestion equipment.

A prior art method for producing a fuel gas from carbonaceous materials, e.g. coal, lignite, peat, etc. is known as high temperature gasification, wherein an oxygen-containing gas is used for burning a portion of the input materials to achieve the necessary minimum gasification temperature of 1500° F.-1600° F. (815° C.-871° C.). The produced syngas typically contains quantities of carbon monoxide CO and hydrogen $H_2$, but a major portion will be carbon dioxide $CO_2$. Water $H_2O$ is also produced. Inasmuch as a significant portion of the produced energetic liquid is water soluble, the water produced in the gasification reactions negatively affects the yield, unless energy is expended to dewater the water-soluble materials. Furthermore, a significant portion of the input carbonaceous material is consumed to produce the high reactor temperature, and cannot be recovered as a fuel. Thus, the efficiency of converting the carbon-containing material to energetic fuel is lower than desired.

The term "volatiles" as used in the fields of combustion and pyrolysis is defined in ASTM D3172: Proximate Analysis. The analytical method comprises drying of the solids and heating in an airtight crucible to a temperature of approximately 1,700° F. (927° C.). The weight loss represents the volatile portion. References to "volatiles" in the remainder of this discussion will use the combustion/pyrolysis definition thereof, i.e. pyrolysis at 1,700° F.

A number of firms, indicated at:
http://www.coskata.com/ and http://www.ineosbio.com/57-Welcome to INEOS Bio.htm are reportedly gasifying waste materials at high temperatures to produce a syngas that has significant fractions of carbon monoxide (CO), hydrogen ($H_2$), and water. After separating out the other components of the syngas, the carbon monoxide, hydrogen and water are fed into a bioreactor where proprietary microorganisms initiate a bacterial fermentation process and eventually produce ethanol. There are a number of issues associated with this process. For example, the ethanol producing organisms are not considered robust.

Pyrolysis is a treatment method in which a substance is changed by subject to heat alone. Pyrolysis differs from gasification in that there is an absence of oxygen. Pyrolysis has been long used for making charcoal from wood. Typically, about 25 to 35 percent of the carbon in wood becomes carbonized, i.e. fixed as charcoal, and the remainder of the wood is converted to gaseous products, e.g. carbon dioxide, carbon monoxide, methane, and hydrogen; and condensable substances including various alcohols, organic acids, ammonia, ketones, phenols, creosote, oils, tars, and water. The manufacture of charcoal has long been accomplished using relatively uncontrolled batch processes. The results have varied, depending upon the heating rate and time, maximum temperature, type of wood, size of wood particles, and other factors.

Since the oil crisis of the 1970's, a number of researchers have attempted pilot scale pyrolysis designed to produce a "bio-oil" from various forms of biomass. High temperature pyrolysis differs from "gasification". In conventional pyrolysis, oxygen is substantially excluded and the operating temperatures to achieve destructive distillation are much lower, typically about 750° F.-800° F. (399° C.-427° C.). The destructive distillation results in a gas, a liquid and solid matter, i.e. char. The combined water/organic liquid product that is condensed out after the pyrolysis or destructive distillation step is known as "pyroligneous acid". The goal of the "bio-oil" process is to eventually produce an oily product that can be burned in a diesel engine. These small plants have suffered and continue to suffer from a number of operational problems. Although under the proper time, temperature and heating rate conditions, the pyroligneous acid may include a phase resembling an "oil-like" substance, it is oxygenated and the oils and other components are partially soluble in the significant quantities of water that are also produced in pyrolysis. The bio-oil is reported to be very corrosive. The heating value of the oily product is relatively low.

Approximately 200 chemical species have been identified in the liquid product from a pyrolysis conversion of biomass to wood vinegar and wood alcohol. The primary species include alcohols such as methanol, butanol, amyl alcohol, etc.; acids such as acetic, formic, propionic, valeric, etc.; bases such as ammonia, methylamine, pyridine, etc.; phenol and phenol-like substances syringol, cresol, etc.; and neutral substances such as formaldehyde, acetone, furfural, valerolactone, etc.

The solid byproducts remaining from pyrolysis of wood are sometimes termed "biochar" or "Terra Preta", and have been found to have agronomically beneficial properties.

Another variant of pyrolysis, generally known as terrefaction, was traditionally used for roasting coffee beans. It involves heating a biomass material to about 200-320° C. (392-608° F.) in an oxygen-free atmosphere for about 30 to 90 minutes. About 70-80 percent of the starting material is converted to a dense solid.

Despite the problems in directly producing a liquid fuel, nearly all current research in pyrolytic fuel production continues to be directed at producing a "bio-oil" for diesel engines from a woody biomass. For example, in U.S. Pat. No. 5,959,167 to Shabtai et al., lignin is converted to oxygenated gasoline compositions by a process including a catalyzed depolymerization, followed by a selective catalytic hydrocracking and an exhaustive etherification reaction.

In U.S. Pat. No. 7,578,927 to Marker et al., substances simulating gasoline and diesel oil are produced by subjecting cellulosic waste to pyrolysis to form a liquid stream and a lignin stream. The separated lignin stream is subjected to a hydrotreating (partial cracking) step at 500-3000 psia to decarboxylate the lignin into oils.

Other approaches to converting biomass to fuels are extant. For example, in U.S. Pat. No. 7,494,637 to Peters et al. and U.S. Pat. No. 5,865,898 to Holtzapple et al., biomass is mixed with a metal oxide and reacted at 1400° C. or higher temperature to form biomass carbides. The product is then quenched to less than 800° C. to form gaseous acetylene.

One approach to resolving the problem created by lignin blockage of celloulosic surfaces is a pre-hydrolysis step to initially dissolve the linkage between lignin and hemicellulose. In U.S. Pat. Nos. 4,880,473; 5,395,455 and 5,605,551 to Scott et al., a process is disclosed for making fermentable sugars from wood which includes a first hydrolysis with sulfuric acid at elevated temperature to dissolve hemicellulose while leaving most cellulose as a solid. The acidified solid phase is then subjected to a very short "flash" pyrolysis of less than 2 seconds at temperatures of 400-600 ° C. The pyrolysis product contains sugars and anhydro-sugars as well as lignin materials. Water is added and the insoluble lignin-containing materials are separated from the soluble aqueous phase containing the fermentable sugars. The method is relatively expensive. Similar hydrolysis methods are disclosed in U.S. Pat. Nos. 5,424,417; 6,002,419, and 6,228,177 of Torget, et al.

In U.S. Pat. No. 7,608,439 to McTavish et al., oxygen-free combustion gases containing carbon dioxide $CO_2$ are fed to an anaerobic digester for conversion of $CO_2$ to methane $CH_4$.

A careful reading of the following description in correlation with the appended drawings of the invention will define the differences of the present invention from prior art processes, and will demonstrate the advantages which are attained thereby.

BRIEF SUMMARY OF THE INVENTION

A general object of this invention is to define a process which will convert a substantial fraction of the ligno-cellulosic material from non-biotreatable or slowly biotreatable compounds into compounds which are readily biotreatable by anaerobic microorganisms.

An object of this invention is to define a process which will substantially increase the overall conversion of ligno-cellulosic materials to fuel gas or ethanol and/or other energetic liquid fuels in a subsequent biological or physical/chemical system. In this invention, direct pyrolytic production of a "bio-oil" is not in view.

Another object of this invention is to define a process whereby waste and low grade materials such as sewage sludge, wood, cellulosic waste, municipal solid wastes (MSW), low grade coal, lignite and other biomaterials may be converted at high efficiency to fuel gases and/or ethanol and/or other energetic liquid fuels or commercial chemicals.

The invention comprises a process for manufacturing energetic fuels from biomass and biomass-derived materials and the like, including high-lignin materials. Such materials include but are not limited to wood, paper, paper mill wastes, sewage sludge, municipal solid wastes, dried plants, sawdust, corn stover, solid wastes from other renewable fuel processes, and the like. As in all industrial processes, the present process will be applied wherever the economic benefit is substantial. The huge supply of lignin-containing materials such as wood and ligno-cellulosic wastes, together with the high cost of fuel, suggest a prime utility of the process, and such use will be described in detail, infra.

The process of the invention may be viewed as having two major steps, i.e. low temperature, extended (long) residence time (LTLT) pyrolization, followed by an anaerobic biotreatment step. Thus, it is designated a pyrobiomethanation treatment method. It is to be understood that in one embodiment, the primary goal of the process is to produce an alcohol such as ethanol, although methane may be co-produced. Within each major step are several sub-steps.

In one embodiment of the instant invention, a ligno-cellulosic material is first subjected to pyrolysis at relatively low temperatures for an extended time period, resulting in conversion of volatile materials to (a) an aqueous "pyroligneous acid" containing organic acids (such as acetic acid), alcohols (principally methanol), and other organic compounds, and (b) a gas stream (pyrogas) containing methane, carbon dioxide, hydrogen, water, and lesser quantities of other volatile organic substances. A residual solid phase primarily comprises char (fixed carbon) and ash.

Following separation of the solid phase from the gas and liquid phases, the liquid phase is subjected to biological treatment by anaerobic methanogenic organisms to produce a mixed gaseous stream of methane and carbon dioxide, useful as an energetic fuel gas. If necessary, toxic materials (typically phenolic materials) may be removed from the "pyroligneous acid" before introduction into the biotreatment step.

Pyrogas formed in the pyrolysis step may be combined with fuel gases formed in the biotreatment step, or may be used separately, or may be introduced into the biotreatment step itself and pass therethrough, increasing the generation of methane gas. Known methods for removing carbon dioxide from the energetic fuel content of the pyrogas and/or biogas may be used to concentrate the fuel gases and reduce carbon dioxide emissions.

In this process, the extended pyrolysis step converts lignin-containing materials which are resistant to biotreatment into liquid materials which are readily bioconverted into fuels. Thus, the result is an enhanced yield of fuel, and a reduction of materials required to be landfilled or otherwise disposed.

In another embodiment of the invention, the pyroligneous acid from the extended pyrolysis step is biotreated by yeast or yeast-like organisms to produce a liquid fuel such as ethanol.

In accordance with a general description of the invention, a biomass-based, ligno-cellulosic material having an inherent fuel value, such as biomass e.g. wood and plants, municipal solid waste (garbage), sewage sludge, and the like, is pyrolized under Low Temperature Long Time (LTLT) conditions. Typically, pyrolysis temperatures between about 175° C. and about 325° C. (about 347° F. to about 617° F.) are utilized, and the residence time is extended, i.e. between about 0.1 hour and about 2.0 hours, depending upon the particle size of the lignocellulosic feed material and the particular operating temperature. For many materials, a pyrolysis residence time of about 0.1 hour to about 0.5 hour is preferred.

A pyrogas is produced, and largely comprises carbon dioxide ($CO_2$), carbon monoxide (CO), hydrogen ($H_2$), and methane ($CH_4$). The condensed liquids from pyrolysis, typically known as "pyroligneous acid", comprise various alcohols, organic acids, ketones, and other organic substances. Residual solids comprise ash, and fixed carbon e.g. charcoal.

The pyrolysis output is cooled and condensed into separate gas, liquid and solid streams. The liquid stream, i.e. pyroligneous acid, may be separated into several phases by gravitation. One or more phase(s) may contain substances toxic to biosystems, and such toxins (such as phenolic materials) may be removed if necessary to ensure rapid biotreatment. Also, depending upon the particular biota and the acidity of the pyroligneous acid, pH adjustment may be necessary.

In an alternative embodiment of the invention, the pyroligneous acid is treated in a substantially anaerobic fermentation step wherein ethyl alcohol (ethanol) is formed. Ethanol is useful as an automotive fuel additive, typically being used at levels up to ten percent.

In one embodiment of the invention, sludge from an anaerobic digester is dewatered and subjected to pyrolysis, producing a pyrogas and a pyroligneous acid. The pyroligneous acid (optionally together with the pyrogas) is recycled to the anaerobic digester to enhance pyrogas production and further reduce the quantity of volatile materials.

The following detailed description of the invention together with the appended figures describe the basic method for achieving the several objects. Several of many possible variations are further described, infra, and will become apparent to those knowledgeable in the art.

DESCRIPTION OF THE PREFERRED EMBODIMENTS

Figure 1:
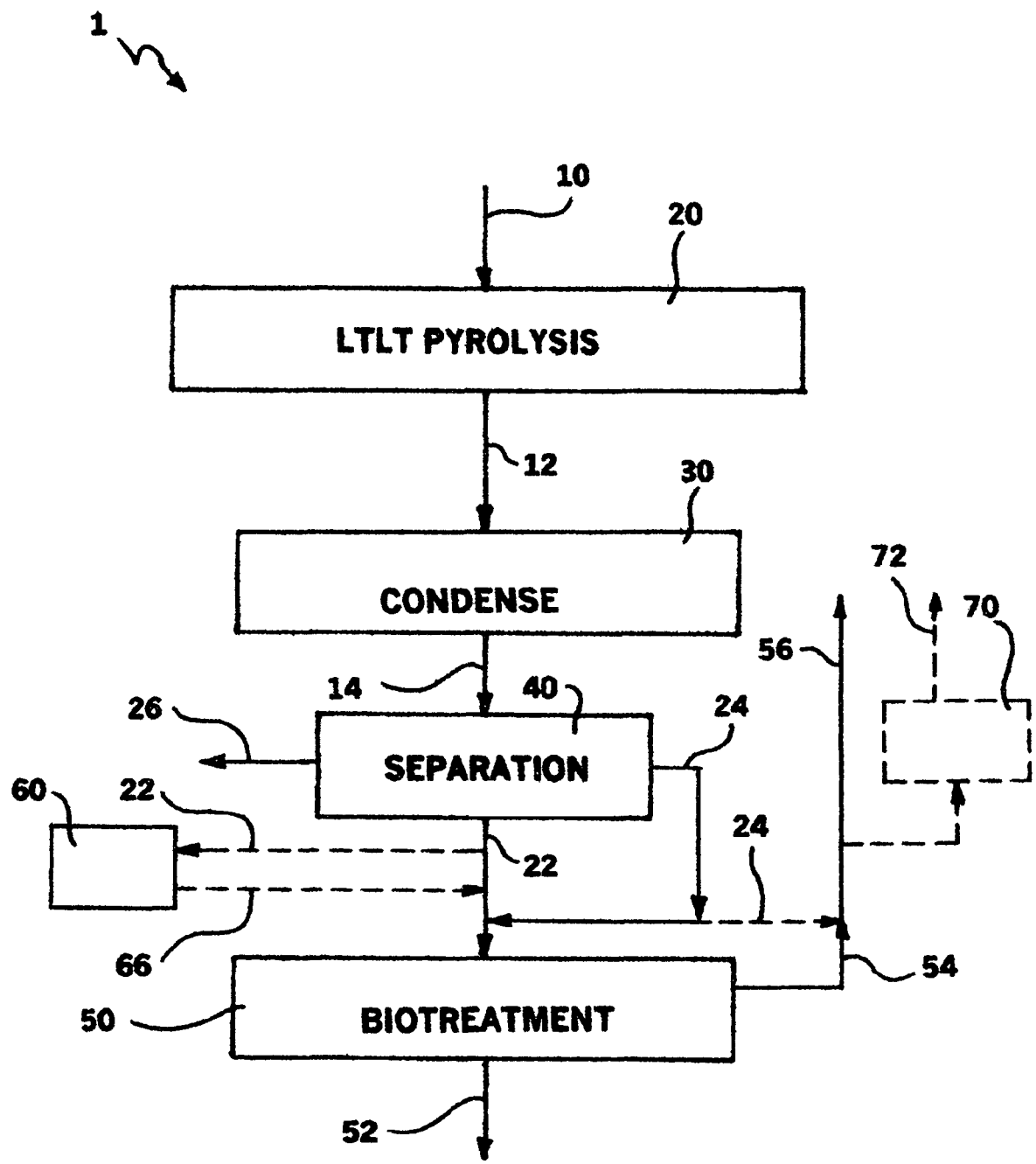
FIG. 1 is a generalized block diagram of a pyrobiomethanation method of the instant invention for treating cellulosic based, lignin bearing materials to produce methane-containing and/or ethanol fuel materials.

As shown in FIG. 1, the invention relates to a pyrobiomethanation process 1 for treating a broad spectrum of biomass based, lignocellulose-bearing materials 10 referred to hereinafter as LCM. Such materials may include, for example, municipal waste materials, e.g. sewage sludges (primary, secondary and digester sludges), solid wastes which contain ligno-cellulosic content, paper mill wastes containing cellulose and/or lignin materials, and the like. For example, LCM materials 10 may comprise plant stalks, hardwoods, softwoods, straw, stover, and the like. LCM materials 10 may also include low grade coals, lignite, peat, etc. The presence of other types of input materials including non-lignin cellulosic materials is not precluded. In fact, the lignin content of these materials may vary widely.

Figure 4:
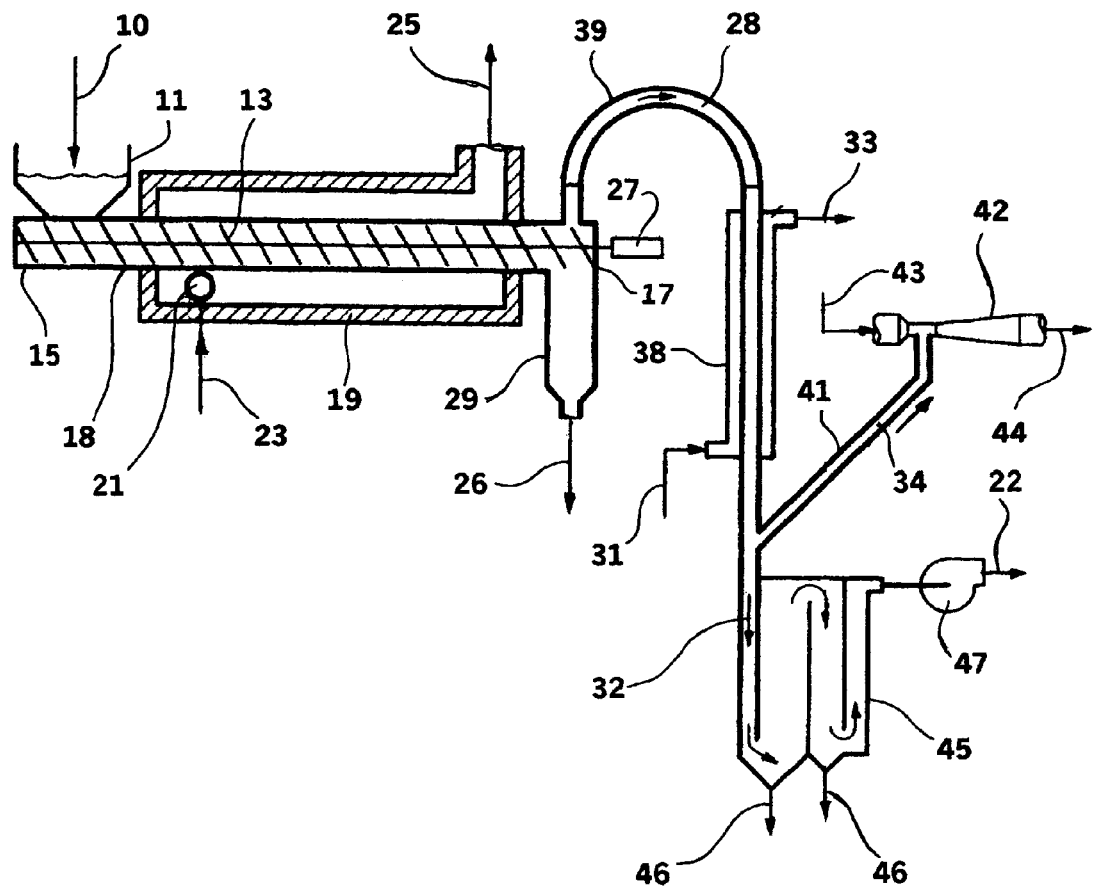
FIG. 4 is a flowsheet showing a system of the invention for treating lignocellulosic materials by pyrolyzing, condensing, and separating pyrolyzed materials into a readily biotreatable liquid stream, a combustible fuel gas, and pyrosolids with reduced volatile matter.

In the method of the invention, the cellulose-containing material 10 is pyrolized to form a liquid containing biotreatable liquid substances which are bio-convertable to useful energetic fuels such as methane-containing fuel gas 52 or ethanol 92 (see FIG. 4). One byproduct of the pyrolysis step 20 is a condensed pyrogas 24 typically containing (dry basis) about 20 to 30 percent methane, butane, and propane, 30 to 40 percent carbon dioxide, 30 to 40 percent other energetic gases (hydrogen and carbon monoxide), and a variable quantity of other volatile organic substances. The term "methane" will be used herein as including other energetic hydrocarbon gases. Residual pyrosolids 26 largely comprise ash and char.

In step 20 of process 1, the biomass based, lignin bearing input materials (LCM) 10 are subjected to pyrolysis, that is, heating in the substantial absence of oxygen, at relatively low temperatures for relatively extended periods. These temperatures are much lower than temperatures required in so-called "bio-oil" processes whose aim is the direct production of fuel oils. Also, unlike the "bio-oil" processes, the pyrolysis residence time conditions of the present method are much longer and are controlled to yield maximum production of soluble "wood alcohol" (typically including methanol, butanol, amyl alcohol, etc.) and soluble "wood vinegar" (typically including acetic acid, formic acid, propionic acid, acetone, ammonia, etc.). The Low Temperature Long Time (LTLT) pyrolysis step 20 results in substantial conversion of volatile materials and lignin present in the LCM 10 to pyroligneous acid 22 and pyrogas 24.

The pyrolysis temperature may vary from about 175° C. to about 325° C. (347° F.-617° F.), which is much lower than the 800° C. to 900° C. (1472-1652° F.) temperatures required in gasification processes. Because of the low pyrolization temperature, the cost of heating the incoming solid materials 10 for pyrolization is much lower than is used in prior art "biogas" processes.

The pyrolization residence time at temperature, generally about 0.1 hours (6 minutes) to about 2.0 hours, is much greater than the short process times found in gasification and bio-oil processes (typically, <2 seconds). The goal is to convert a major portion of the lignin to methane and soluble substances. The residence time, while extended, is particularly dependent upon the particle size of incoming solid materials 10 due to heat transfer and mass transfer considerations. As would be expected, for example, the pyrolysis residence time for processing large blocks of wood is necessarily greater than for processing particles of sawdust size or even smaller particles such as found in municipal sewage sludges. For example, for lignocellulosic materials 10 of sawdust size or smaller, the preferred pyrolysis residence time is about 0.1 hour to about one (1.0) hour. Also, the optimum operating temperatures and residence times will vary, depending upon the composition and chemical structures of the materials 10 being pyrolyzed, including the quantity of lignin accompanying cellulose. For many biomass materials, a preferred pyrolysis residence time is about 0.1 hours to about 0.5 hours.

The pyrolized materials 12 from step 20 are cooled and condensed in condense step 30 to produce cooled product mixture 14 which is separated into gas, liquid and solid phases in phase separation step 40. The separate streams which are produced include (a) liquid pyroligneous acid 22, (b) a mixture of non-condensable gases, i.e. pyrogas 24, and (c) pyrosolids 26 largely comprising fixed carbon and ash, together with any residual lignin-containing materials.

The pyroligneous acid 22 is typically multi-phase comprising wood alcohol, wood vinegar and water (both pyrolysis-produced and in the input materials 10) as well as smaller quantities of wood tar, pitch, and light oil, which may be separated from the water-soluble components by gravity. If necessary, the pyroligneous acid 22 from phase separation step 40 may be further treated in step 60 to remove substances which are toxic to biological growth. Such treatment is shown as resulting in an enhanced pyroligneous acid 66. Treatment 60 may include pH adjustment if beneficial to the subsequent biotreatment step 50.

The pyrogas 24 comprises carbon dioxide $CO_2$, carbon monoxide CO, hydrogen $H_2$, and methane $CH_4$. The latter three gases are all combustible gases useful as fuel. Pyrogas 24 may be removed and used apart from the process L or may pass together with pyroligneous acid 22 to biotreatment step 50. Also, pyrogas 24 may alternatively be joined with biogas 54 (largely methane) formed in the biotreatment step 50, to form a combined fuel gas stream 56.

The pyrosolids 26 may be used as a soil-enhancing additive useful in agronomy. In the case where the pyrosolids 26 are required to be land-filled, the present invention significantly reduces the quantity thereof and associated disposal costs.

As shown in FIG. 1, the condensed pyroligneous acid 22 is shown as being passed to biotreatment step 50. The pyroligneous acid 22 containing a substantial quantity of soluble "wood alcohol" and "wood vinegar" is, in one embodiment of this invention, subjected to anaerobic digestion with methanogenic microorganisms to produce methane-rich fuel gas, i.e. biogas 54.

Figure 3:
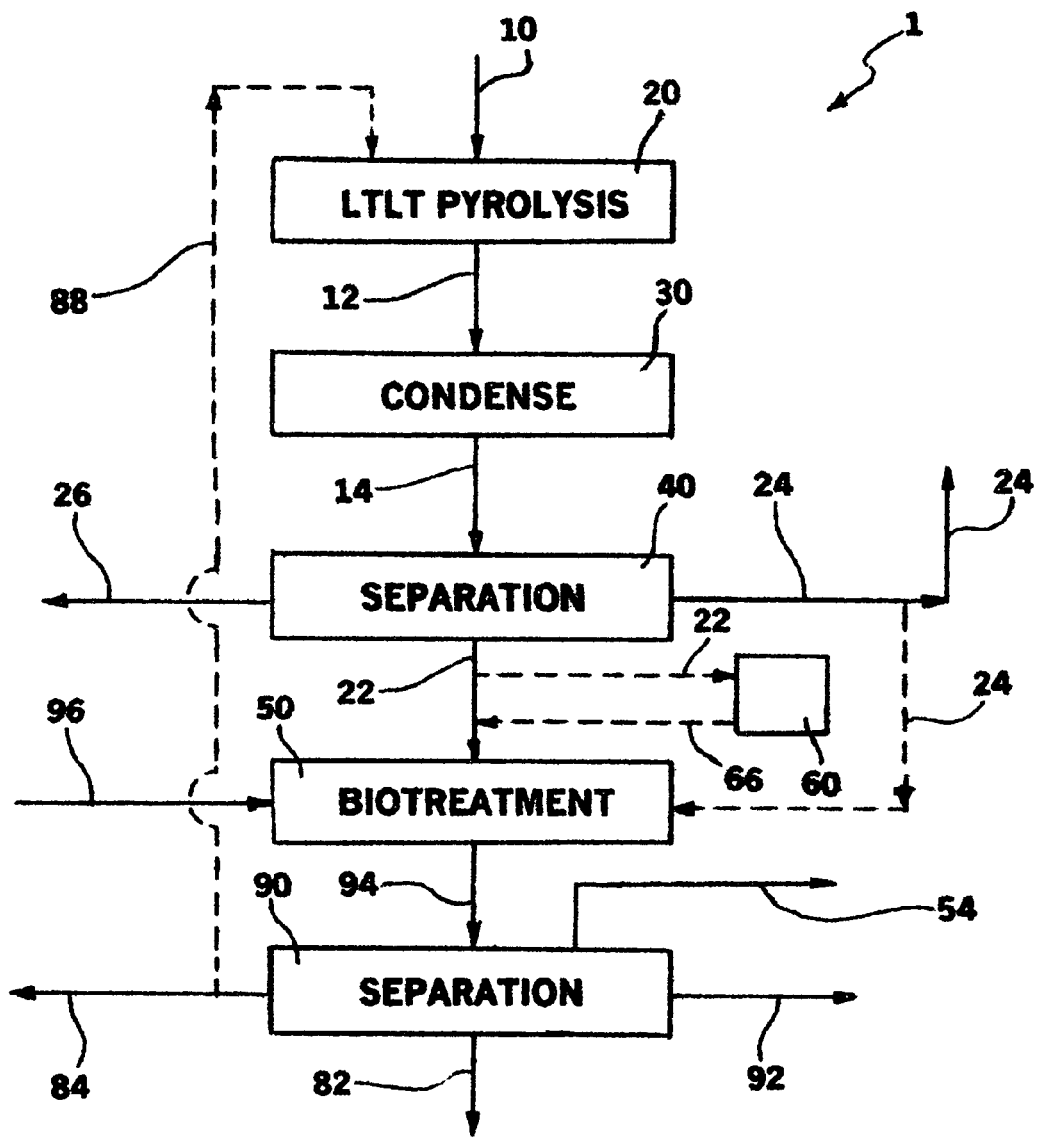
FIG. 3 is a generalized block diagram illustrating a pyrobiomethanation method of the invention for treating cellulosic based, lignin bearing materials to produce ethyl alcohol.

Alternatively, the pyroligneous acid 22 may comprise a feed material to an oxygen-starved fermentation with specific microorganisms which produce ethanol 92 (see FIG. 3). Such a process is described in more detail, infra.

In the process illustrated in FIG. 1, the removal of volatile matter from the incoming materials (LCM) 10 will be significantly increased above the low conversion achieved in direct anaerobic digestion of such materials. The product formed from the volatile matter in the biotreatment step 50 is primarily a methane-bearing digester gas, i.e. biogas 54 of about 65% methane ($CH_4$) and 35% carbon dioxide ($CO_2$). Some of the volatile matter is converted to additional micro-organisms and associated biological materials. Typically, a reduction of 1.0 kg. of volatile matter will produce about 0.6 kg. of biogas 54, dry basis, containing about 0.39 kg. methane. The unpurified biogas 54 or combined fuel gas 56 may be concentrated by nearly quantitative removal of its carbon dioxide content by various methods 70 well known in the art, to produce a heating gas 72 of heating value of 970-990+ BTU per standard cubic foot. Where required by statute, siloxanes, hydrogen sulfide, or other compounds may also be removed. The residual undigested solids from the biotreatment step are shown as biosolids 52.

Thus, as a result of process 1 of the invention, the fraction of ligno-cellulosic materials 10 which is converted to useful high energy substances is significantly enhanced, i.e. the overall efficiency is increased. In the treatment of waste treatment sludges and solid waste materials, the quantity of materials which require land-filling or other costly processing is substantially reduced. The process is particularly useful in the treatment of ubiquitous low-value cellulosic materials to produce feedstocks for creation of valuable fuels by biotreatment processes.

Variations of the process of method 1 may be used in particular circumstances without deviating from the basic concepts thereof. For example, the steps of a preferred embodiment of the invention are depicted in FIG. 2 for the enhancement of anaerobic digestive treatment of municipal sewage sludge and the like.

Figure 2:
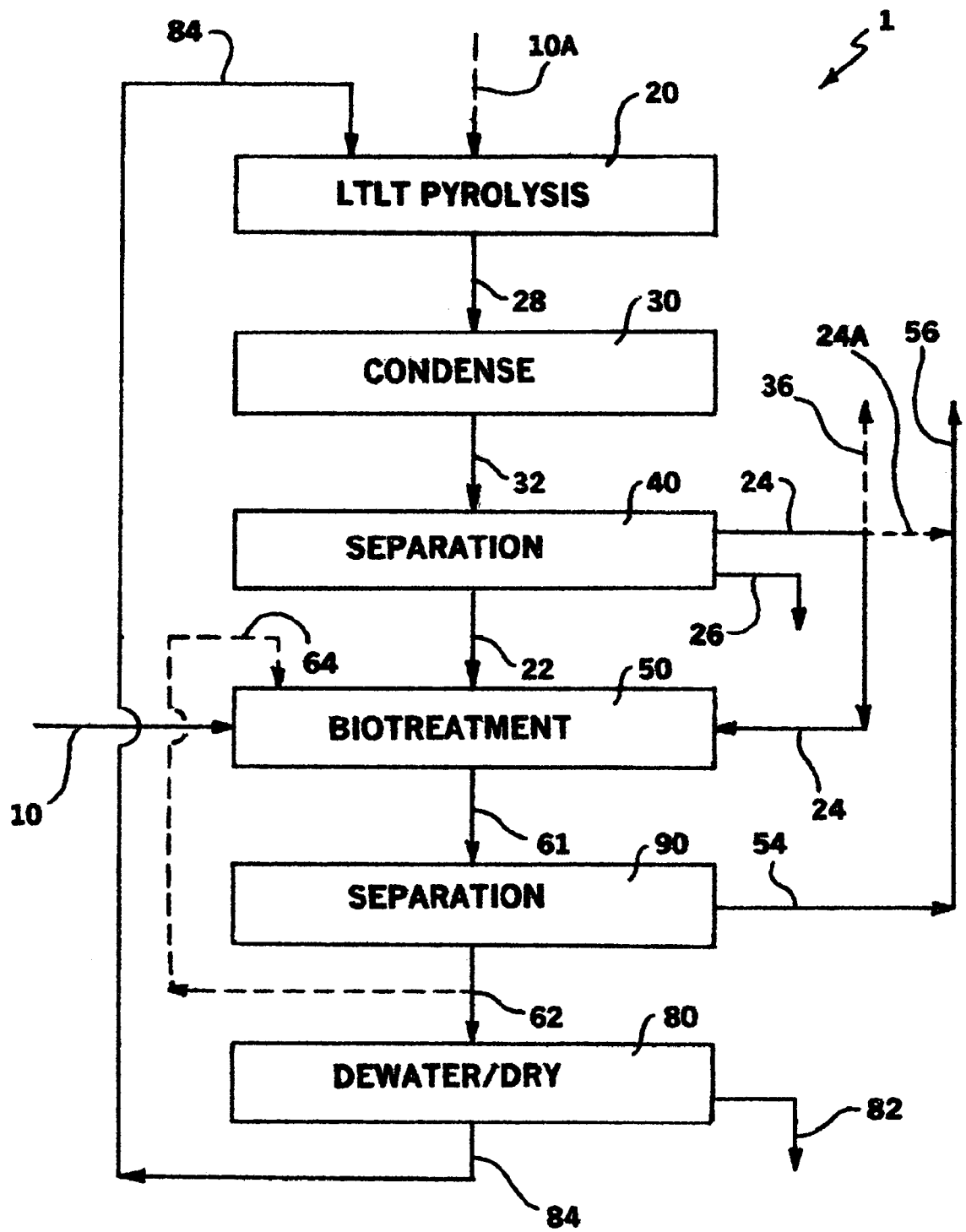
FIG. 2 is a generalized block diagram illustrating a pyrobiomethanation method of the invention for enhancing the production of methane from sewage sludge and the like in an anaerobic digester.

As shown in FIG. 2, a ligno-cellulosic containing material (LCM) 10 such as sewage sludge is first subjected to biotreatment i.e. anaerobic methanogenic digestion 50 in an aqueous system. The incoming material 10 may be, for example, either sludge solids settled out of raw sewage i.e. "primary sludge", settled biological solids from a secondary system, e.g. "activated sludge", or a combination thereof. Methane rich biogas 54 is produced and separated in step 90 from the remaining aqueous mixture 62, also known as "digester sludge". The latter is dewatered (and optionally further dried) in dewater/dry step 80, wherein water 82 is expelled therefrom.

The dewatered solids 84, are then passed to a low temperature, long time (LTLT) pyrolization step 20, wherein a portion of the volatile solids therein is converted to a fuel-rich gas. Also produced is a condensable mixture of alcohols, acids, etc. as previously described, and residual pyrosolids. As shown, the pyrolysis product 28 of gas, liquid and solids is cooled and condensed in step 30 to form condensed product 32 and separated in phase separation step 40 into (a) pyrogas 24, (b) liquids known collectively as pyroligneous acid 22, and (c) pyrosolids 26 which may include tars and ash.

As shown in FIG. 2, the pyroligneous acid 22 is then fed to biotreatment, i.e. anaerobic digestion step 50. Preferably, pyrogas 24 is also introduced into the biotreatment step 50 to enhance mixing therein and biogas production. Thus, the biogas 54 leaving the biological treatment step 50 is actually the total of biologically produced gas and pyrogas 24 from the pyrolysis step 20. In this way, volatile solids in the bio-produced sludge 62 are repeatedly, sequentially subjected to pyrolysis step 20 and biotreatment step 50 to maximize both fuel gas production and the reduction in volatile solids. Ash initially present in the incoming LCM 10 is continually removed from the system as pyrosolids 26. In most cases, a portion 64 of the bio-produced sludge 62 may be recycled to the biotreatment step 50 to maintain a desired population of methanogenic anaerobes therein. Pyrogas 24 may optionally be directed as stream 24B to be injected into recycled sludge portion 64 and thus be introduced into the biotreatment step 50 to enhance mixing and resultant methane production.

Optionally, only a portion (or even none) of the pyrogas 24 may be introduced into the biotreatment step 50. Thus, a portion or all of pyrogas 24 may instead be directed as stream 24A to be combined with biogas 54 to form combined fuel gas stream 56. Alternatively, a portion or all of pyrogas 24 may be separately removed from the system as stream 36. As previously shown in FIG. 1, the net produced gas stream 56 and/or 36 may be purified to produce an enhanced fuel gas 72 with high heating value.

Also, recycle of other streams may be practiced in accordance with the invention. For example, a portion of pyrosolids 26 from separation step 40 may be recycled to the pyrolysis step 20 for further conversion into pyrogas 24 and pyroligneous acid 22.

In this system, additional pyrogas 24 and biogas 54 may be produced by feeding additional lignocellulosic material(s) 10A to pyrolysis step 20. These materials 10A may comprise, for example, plant stalks, wood, municipal solid wastes, and various other materials previously described as lignocellulosic materials 10. Materials 10A may include substances which are non-lignocellulosic.

This invention is based on the discovery of the particular conditions of pyrolytic treatment of lignocellulosic material 10 whereby an advantageous synergistic relationship is established between pyrolization and subsequent biotreatment. As a result of process 1 of the invention, the fraction of lignocellulosic materials which is converted to useful high energy substances is significantly enhanced, i.e. the overall efficiency is increased. In the treatment of waste treatment sludges and solid waste materials, the quantity of materials which require land-filling or other costly processing is reduced or even eliminated. The fraction of volatile solids which remain in the recovered pyrosolids 26 is substantially reduced. As is evident, while water production in prior art gasification processes results in reduced yields, water production in pyrolyzation of the present invention provides the aqueous medium for solubilizing the incoming materials 10. Thus, it is an advantage which enhances overall efficiency.

In another embodiment of the invention, the biotreatment step 50 comprises an oxygen-limited or oxygen-starved (i.e. anaerobic) fermentation using microorganisms specific to production of ethyl alcohol (ethanol). Turning now to FIG. 3, an exemplary process 1 of this embodiment is shown as including the steps of (a) low temperature, long time (LTLT) pyrolysis 20 of an incoming lignocellulose-containing material 10, (b) condensation 30 of the pyrolyzed materials 12, (c) phase separation 40 of the cooled and condensed pyrolysis materials 14, (d) oxygen-starved biotreatment (fermentation) 50 of the liquid condensate, i.e. pyroligneous acid 22 and (e) separation 90 of the fermented materials 94 to produce the desired concentration of the desired product ethanol 92. Several separation sub-steps may be required to achieve the desired purity of ethanol.

In this embodiment, the pyrolysis step 20 is conducted under low temperature, long time conditions as previously described, and following condensation (step 30) and phase separation (step 40), produces aqueous pyroligneous acid 22, a pyrogas 24, and pyrosolids 26 containing ash, char, tar and other settleable solids. In FIG. 3, the pyrogas 24 is shown as being recovered as a useful fuel, or alternatively, first passed to the biotreatment step 50 to enhance mixing and/or to be partially consumed in the fermentation to produce additional ethanol 92. The biotreatment step 50 may be augmented with various media ingredients 96 including vitamins and minerals to achieve a desired high ethanol production. Such ingredients 96 may include for example, saccharified materials and mineral salts. The pyroligneous acid 22 containing wood alcohol and wood vinegar will provide a substantial portion of the ethanol substrates, however. If desired, the pyroligneous acid 22 may be further treated in step 60 before it is introduced as treated pyroligneous acid 66 into the biotreatment step 50.

In separation step 90, the desired product ethanol 92 is separated from water 82, offgases 54 and biological solids 86. The biological solids 86 may be utilized as an agronomical supplement, or as shown in FIG. 3, recycled as stream 88 to the pyrolysis step 20 for conversion to additional pyroligneous acid 22 and pyrogas 24. The off-gases 54 i.e. biogas typically contain a substantial portion of $CO_2$, and will, if pyrogas 24 is directed to the biotreatment step 50, also contain substances thereof not consumed in the biotreatment step 50.

Pyrolysis, condensing, phase-separation, and biological treatment equipment of varied types known in the art may be used for each of the steps of this invention. To achieve uniform results, the pyrolysis equipment should be capable of temperature control and residence time control.

FIG. 4 illustrates a preferred embodiment of the means for accomplishing the pyrolization step 20, subsequent condense step 30 and separation step 40. Exemplary pyrolizer 18 is shown as a kinetic helix pyrolysis reactor with an internal rotatable screw 13 extending generally from a first end 15 to a second end 17. The screw 13 is shown as being rotatively driven by motor 27. The pyrolizer 18 is depicted with a jacket 19 through which hot flue gases 25 generated by burner 21 flow. Incoming lignin-containing cellulosic materials 10 from hopper 11 are transported by rotating screw 13 at a speed which achieves the desired residence time. The hot flue gases 25 from the combustion of burner fuel 23 are controlled to heat the incoming materials 10 to the desired pyrolization temperature. Thus, the transported materials 10 are pyrolized at elevated temperatures to form a mixture 28 of both non-condensable gases and condensable gases which pass through conduit 39. Mixture 28 is cooled and the condensable gases condensed in condenser 38. The condenser 38 is depicted as comprising a cooling jacket through which cooling water 31 flows to indirectly cool the gas mixture 28 by indirect heat transfer. Heated cooling water 33 may be reused as a heat source as desired. Alternatively, water 31 may be directly injected into the gas mixture 28 for cooling. However, such cooling will significantly dilute the pyroligneous acid 22.

The phase separation step 40 actually occurs at three locations in this particular equipment. As shown in FIG. 4, initial separation of gases 28 from ash and char, i.e. pyrosolids 26 occurs at the second end 17 of the pyrolyzer 18, where pyrosolids 26 are discharged from ash collector 29. Following cooling of the mixed gases 28 the non-condensed portion denoted herein as pyrogas 34 is separated from the condensed product 32 and directed in conduit 41 to a biotreatment step 50 as previously described. In this particular embodiment, the pyrogas 34 is shown as being injected into a stream 43 of recycled biosolids before being returned to biotreatment step 50 as mixed stream 44. The biotreatment step 50 may be an anaerobic sludge digestion or ethanol fermentation, for example. In this embodiment, the pyrogas 34 acts as a mixing agent within the biotreatment step 50. Alternatively, the pyrogas 34 may be simply injected directly into the biotreatment step 50, or even mixed with pyrogeneous acid 22 (see infra)

which is to be biotreated. In another embodiment, the pyrogas 34 is used as a fuel without passing through the biotreatment step 50.

The condensed product 32 largely comprises liquids and usually contains certain compounds which solidify due to cooling in condenser 38. In FIG. 4, the condensed product 32 is shown as being passed through a settling device 45 where solids settle out and are collected as one or more streams 46 of tar and other solids. Thus, a third portion of separation step 40 occurs in settling device 45. The liquid portion from the settling device 45, designated as pyrogeneous acid 22, is directed to the biotreatment step 50 as previously described, for example by pump 47.

It is noted that the types of apparatus for pyrolysis, condensing and separation shown in FIG. 4 are representative of a particular embodiment for performing the LTLT pyrolysis step 20 and should not be considered as limiting the invention. Thus, for example, while FIG. 4 depicts pyrolizer 18 as having a kinetic helix construction, other types of pyrolizer construction may be used to practice the instant invention. Well-known designs of hopper 11 and pyrolizer 18, as well as operation methods therefor are utilized for preventing escape of gas mixture 28 from, or air into, the inlet end 15 thereof. While no apparatus is shown for maintaining a constant pressure within pyrolizer 18, pressure control apparatus may be used if desired. Normally, however, the internal pressure will not vary from atmospheric enough to affect the chemical transformation within pyrolizer 18.

EXAMPLES

The advantages of the method of this invention are exemplified relative to a new or existing municipal wastewater treatment plant operating with anaerobic digestive biotreatment of primary and secondary i.e. activated sludges, as depicted in FIG. 2.

A material balance based on reasonable values of conversion in a continuous system 1 is presented as follows, where flow rates are in pounds per hour. Several cycles of the method will be shown to provide a distinct advantage, with a maximum benefit derived under steady state conditions. It is understood that the system 1 may alternatively be operated as a batch system in any or all of steps 20, 30, 40, 50, 80, and 90.

Incoming lignocellulose-bearing material 10 comprising sewage sludge is represented as 2000 pounds per hour of total solids, of which 1500 pounds/hour is volatile i.e. combustible, and 500 pounds/hour is non-volatile ash. In anaerobic biotreatment step 50 the conversion of volatile solids is assumed to be 45.0 percent. Biotreatment 50 followed by separation in step 90, results in about 675 pounds/hour of digester gas 54, 825 pounds/hour of ungasified volatile solids and 500 pounds/hour of ash in aqueous stream 62. Stream 62 is dewatered to about 92% solids in dewater/dry step 80 and subjected to LTLT pyrolysis in step 20. Digester gas 54 from biotreatment step 50 contains about 65% methane, i.e. 438 pounds/hour.

Dewatered solids 84 are converted in LTLT pyrolysis step 20 to a mixture 28 which, when condensed in step 30 and separated in step 40 results in 248 pounds/hour pyrogas 24, 601 pounds/hour of condensed pyroligneous acid 22, and 583 pounds/hour of insoluble solids 26. The latter comprises 500 lbs/hr ash and 83 lbs/hr fixed carbon. The insoluble solids 26 may be used as a soil amendment for agronomic enhancement, either before or after drying/dewatering.

The pyroligneous acid 22 from the LTLT pyrolysis step 20 comprises 248 lbs/hr of soluble organic liquids (volatile matter), 106 lbs/hr of water from the incoming stream 84, and an additional 248 lbs/hr of water produced by pyrolytic reactions. The pyroligneous acid 22 is directed to biotreatment step 50 where it is substantially converted to 248 pounds/hour of digester gas (in addition to that derived from the sludge 10).

The 248 pounds/hour of pyrogas 24 are directed to biotreatment step 50. In this analysis, it is assumed that pyrogas 24 passes through the biotreatment step 50 without chemical change and becomes mixed with the biologically produced gas to become mixed fuel gas 54. Mixed fuel gas 54 is thus a mixture of (a) 675 pounds/hour of biologically produced gas derived from sludges 10, (b) 248 pounds/hour of biologically produced gas derived from pyroligneous acid 22, and (c) 248 pounds/hour of pyrogas 24 produced from pyrolysis of dewatered biotreatment solids 84.

Thus, by introducing an LTLT pyrolysis step to the treatment of sludges, the calculated overall gas production from sludges 10 is increased by about 73.5 percent. The net production of energetic gases methane, hydrogen, and carbon monoxide is increased by about 59.4 percent. The conversion of volatile solids in incoming sludges 10 to gases is approximately doubled from 45.0 percent to about 90+ percent. In addition, the remaining insoluble solids 26 may be used as a beneficial soil amendment, avoiding the use of landfill entirely.

An additional benefit of a preferred embodiment of the invention relates to governmental permitting requirements for gas discharges. Inasmuch as all gases from the pyrolysis step 20 are introduced into the biotreatment step 50 as a feedstock thereto, it may be argued that no separate air quality discharge permit is required for the pyrogas 24.

Thus far, we have not considered the possibility of adding an undigested lignocellulosic material to the LTLT pyrolysis step 20. For example, a lignocellulosic material 10A such as wood may be fed to pyrolysis step 20 at an exemplary 1000 dry pounds/hour of volatile matter. LTLT pyrolysis of this material will produce about 300 pounds/hour additional pyrogas 54 and about 300 pounds/hour additional soluble organic liquids in the pyroligneous acid 22. The resulting overall production of combined gas 54 from pyrolysis and digestion is, in this example, increased by about 600 pounds/hour, an additional 88.9 percent when compared to pyrobiomethanation treatment of lignocellulosic material i.e. sludges 10 only. Thus, methane-containing energetic fuel gases may be readily produced from lignocellulosic waste materials and/or ubiquitous natural cellulose-containing materials. Because of the low pyrolysis temperatures, energy derived from the produced fuel gases exceeds the energy required by the process 1 of the invention.

Turning now to another utility of the invention, which is the production of a precursor for ethanol production by LTLT pyrolysis of lignocellose-bearing materials. An example is presented based on a flowsheet shown in FIG. 3.

As previously noted, a first step 20 of LTLT pyrolysis of a lignocellulose-bearing material 10 produces a mixed stream 12 which after condense step 30 and separation step 40, results in a liquid pyroligneous acid 22 comprising wood vinegar and wood alcohol, and a pyrogas 24 containing methane, hydrogen, carbon monoxide and carbon dioxide. A pyrosolids stream 26 of solid and semisolid materials is largely comprised of ash and char.

The organic substances in pyroligneous acid 22 are utilized as starting materials for the production of ethanol in biotreatment step 50. The industrial scale production of ethanol by yeasts and other microorganisms is well-known, utilizing a variety of starting substrate materials. The utilization of pyroligneous acid 22 from the instant LTLT pyrolysis process reduces the raw material cost for ethanol fermentation and may reduce treatment costs of waste materials.

It is evident to those skilled in the art that various changes and modifications may be made in the methods and apparatus of the invention as disclosed herein without departing from the spirit and scope of the invention as defined in the following proposed claims.

What is claimed is:

1. A method for converting a wastewater treatment sludge in a biotreatment process to produce a methanaceous fuel gas, comprising:
    treating said sludge by way of anaerobic biological treatment step to produce a methanaceous fuel gas and a dewatered solids stream;
    subjecting said dewatered solids stream to pyrolysis to produce (a) a pyroligneous liquid containing biotreatable liquid substances, (b) a pyrogas, and (c) pyrosolids including char;
    separating said pyrosolids from said pyroligneous liquid and pyrogas; and
    subjecting said pyroligneous liquid to said anaerobic biological treatment step to produce additional methanaceous fuel gas.

2. A method in accordance with claim 1, wherein said pyrolysis is conducted at a temperature of between about 175 ° C. and about 325 ° C.

3. A method in accordance with claim 1, wherein said pyrolysis is conducted with a solids residence time of about 0.1 hour and about 2 hours.

4. A method in accordance with claim 1, wherein said pyrolysis is conducted with a solids residence time of about 0.1 hour and about 0.5 hour.

5. A method in accordance with claim 1, wherein said anaerobic biological treatment step is conducted with methanogenic microorganisms.

6. A method in accordance with claim 1, wherein at least a portion of said pyrogas is introduced into said anaerobic biological treatment step.

7. A method in accordance with claim 1, wherein a major portion of said pyrogas is introduced into said anaerobic biological treatment step.

8. A method in accordance with claim 1, wherein said separated pyrosolids are used as an agronomic soil amendment.

9. A method in accordance with claim 1, wherein said method further includes a step of removing toxic substances from said pyroligneous acid before introduction into said biological treatment step.

10. A method in accordance with claim 1, wherein said method includes a further step of adding at least one of a sugar and vitamins and minerals to said biological treatment step.

11. A method in accordance with claim 1, further comprising a step of adding municipal solid waste to said pyrolysis step.

12. A method for treating lignocellulose-containing material, comprising the steps of:
    introducing lignocellulose-containing material to an anaerobic biotreatment step wherein methanogenic microorganisms produce a methane-containing biogas and an aqueous stream containing residual biosolids;
    dewatering said residual biosolids;
    subjecting said residual biosolids materials to a pyrolysis to produce a pyrolysis product comprising a pyrogas;
    introducing at least a portion of said pyrogas to said anaerobic biotreatment step, wherein said introduced pyrogas portion mixes with said biogas produced in said anaerobic biotreatment step; and
    separating and removing said mixed pyrogas and biogas for use as a fuel gas.

13. A claim in accordance with claim 12, wherein said pyrolysis is conducted at a temperature of about 175 ° C. to about 325 ° C.

14. A claim in accordance with claim 12, wherein said pyrolysis is conducted with a solids residence time of about 0.1 hour to about 2.0 hours.

15. A claim in accordance with claim 12, wherein said pyrolysis is conducted with a solids residence time of about 0.1 hour to about 0.5 hours.

* * * * *